(12) United States Patent
Nagashima et al.

(10) Patent No.: US 6,613,933 B1
(45) Date of Patent: Sep. 2, 2003

(54) PROCESS FOR SEPARATING AND PURIFYING ASPARTAME AND A DERIVATIVE THEREOF

(75) Inventors: Kazutaka Nagashima, Kanagawa-ken (JP); Akihiro Kishishita, Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 183 days.

(21) Appl. No.: 09/590,690

(22) Filed: Jun. 9, 2000

Related U.S. Application Data

(63) Continuation of application No. PCT/JP98/05533, filed on Dec. 7, 1998.

(30) Foreign Application Priority Data

Dec. 11, 1997 (JP) .............................................. 9-340939

(51) Int. Cl.⁷ .......................................... C07C 229/00
(52) U.S. Cl. .......................................... 560/40; 560/41
(58) Field of Search ..................................... 560/40, 41

(56) References Cited

U.S. PATENT DOCUMENTS

| | | | |
|---|---|---|---|
| 3,833,554 A | | 9/1974 | Ariyoshi et al. |
| 5,057,415 A | * | 10/1991 | Sheutz et al. |
| 5,480,668 A | | 1/1996 | Nofre et al. |
| 5,510,508 A | | 4/1996 | Claude et al. |
| 5,728,862 A | | 3/1998 | Prakash |

FOREIGN PATENT DOCUMENTS

| | | | |
|---|---|---|---|
| ES | 2068763 A1 | * | 4/1995 |
| JP | 49-7245 | | 1/1974 |
| JP | 8-503206 | | 4/1996 |
| JP | 10-248520 | | 9/1998 |
| JP | 10-248521 | | 9/1998 |
| WO | WO 95/30689 | | 11/1995 |
| WO | WO 98/32767 | | 7/1998 |
| WO | WO 98/39979 | | 9/1998 |

OTHER PUBLICATIONS

Casillas et al, The Use of Modified Divinylbenzene–Polystyrene Resins in the Separation of Fermentation Products. A Case Study Utilizing Amino Acids and a Dipeptide., Journal of Chemical Technology and Biotechnology 1991, 55(2), pp. 163–169.*

Properties of Synthetic Adsorbents printed from: http://www.diaion.com/Sepabeads_Table_R_E.html.*

U.S. patent application Ser. No. 09/707,953, filed Nov. 8, 2000, pending.

U.S. patent application Ser. No. 09/707,954, filed Nov. 8, 2000, pending.

U.S. patent application Ser. No. 09/708,006, filed Nov. 8, 2000, pending.

U.S. patent application Ser. No. 09/708,007, filed Nov. 8, 2000, pending.

U.S. patent application Ser. No. 09/590,690, filed Jun. 9, 2000, pending.

U.S. patent application Ser. No. 09/590,690, filed Jun. 9, 2000, pending.

U.S. patent application Ser. No. 09/591,562, filed Jun. 13, 2000, pending.

R.–H. Mattern, et al., Journal of Peptide Research, vol. 50, No. 4, pp. 286–299, "Conformational Analysis of Potent Sweet Taste Ligands by Nuclear Magnetic Resonance, Computer Simulations and X–Ray Diffraction Studies", Oct. 1997.

M. Goodman, et al., Journal of Peptide Science, vol. 4, No. 4, pp. 229–238, "X–Ray Structures of New Dipeptide Taste Ligands", Jun. 1998.

* cited by examiner

*Primary Examiner*—Samuel Barts
*Assistant Examiner*—Paul A. Zucker
(74) *Attorney, Agent, or Firm*—Oblon, Spivak, McClelland, Maier & Neustadt, P.C.

(57) ABSTRACT

A process for easily and efficiently separating aspartame (APM) from N-[N-(3,3-dimethylbutyl)-L-(α-aspartyl]-L-phenylalanine methyl ester (APM derivative), and thus separating and purifying the APM and the above-mentioned APM derivative, more specifically the N-(3,3-dimethylbutyl)-APM each at a high purity, which comprises subjecting an aqueous solution containing the APM and the APM derivative, to column chromatography using a nonpolar highly porous polymer based resin.

14 Claims, No Drawings

PROCESS FOR SEPARATING AND PURIFYING ASPARTAME AND A DERIVATIVE THEREOF

This application is a Continuation of international PCT application PCT/JP98/05533, filed on Dec. 7, 1998.

BACKGROUND OF THE INVENTION

1. Field of the Invention

The present invention relates to a process for separating and purifying two sweetening substances of aspartame (APM) and N-[N-(3,3-dimethylbutyl)-L-(α-aspartyl]-L-phenylalanine methyl ester, which hereinafter may be referred to as "N-(3,3-dimethylbutyl)-APM" or "APM derivative", by separating the two substances from each other.

2. Description of the Background

In recent years, eating habits have improved as awareness of obesity caused by excessive sugar intake and diseases accompanied by fatness has increased. Accordingly, the development of a low-calory sweetening agent (sweetener) that replaces sugar has been in demand. As a sweetening agent that is widely used at present, there is aspartame (APM) which is excellent in safety and quality of sweetness. However, the stability thereof remains problematic.

Under these circumstances, French Patent No. 2697844 describes the evaluation of derivatives in which an alkyl group is introduced on an amino group of aspartic acid constituting the APM in one approach to improve slightly the stability and to improve the sweetening potency. N-(3,3-dimethylbutyl)-APM is noted as markedly improving in the sweetening potency. For the production of N-(3,3-dimethylbutyl)-APM, a process for alkylating APM reductively under the coexistence of 3,3-dimethylbutylaldehyde with sodium cyanoborohydride in methanol (refer to the abovementioned FR 2697844 specification), and a process for alkylating APM reductively under the coexistence of 3,3-dimethylbutylaldehyde with platinum carbon as the catalyst in a mixed solvent of water and methanol at a pH value in a range of 4.5 to 5 (WO95/30689) are known. However, when a reaction is carried out according to the processes described in these patent specifications, 3,3-dimethylbutylaldehyde and APM are either both unreacted, or N,N-di(3,3-dimethylbutyl)-APM, produced as a by-product, wherein two alkyl groups have been introduced thereto, are mixed in the reaction solution (mixture) or the crude crystals of the product, to no small extent.

Among the compounds described, 3,3-dimethylbutylaldehyde is removed by drying under reduced pressure or washup with comparative ease, because it has a low boiling point or is soluble in a poor solvent for the N-(3,3-dimethylbutyl)-APM, such as hexane. On the other hand, it is difficult to remove APM and N,N-di(3,3-dimethylbutyl)-APM by crystallization from the residue from which the catalyst and the like have been removed as described in the above-mentioned patent specifications. Hence, the yield thereof is much reduced in order to obtain N-(3,3-dimethylbutyl)-APM having a satisfactory purity. In addition, the N,N-di(3,3-dimethylbutyl)-APM can not be recovered and used for the starting material, or etc., and therefore it is desired to suppress its production to the utmost. Since 3,3-dimethylbutylaldehyde is also problematic in odor (smell), it is desired to consume out the aldehyde as much as possible during the reaction. As one method of solving such an exhaust problem, a process for reacting APM with 3,3-dimethylbutylaldehyde in an excess of APM to the quantity of the aldehyde used might be considered. In such a case, where APM (unreacted) remains in the reaction solution (mixture), it would be desirable to establish a process for easily and efficiently separating APM from N-(3,3-dimethylbutyl)-APM, and thus separating and purifying each at a high purity. Unfortunately, such a process remains elusive.

SUMMARY OF THE INVENTION

Accordingly, it is an object of the present invention to provide a process for easily and efficiently separating the aspartame (APM) from N-(3,3-dimethylbutyl)-APM, and thus separating and purifying the two compounds each at a high purity, from an aqueous solution containing the APM and the N-(3,3-dimethylbutyl)-APM.

The above object and others are provided by a process for separating and purifying APM and N-[N-(3,3-dimethyl)-L-α-aspartyl]-L-phenylalanine methyl ester, which entails subjecting an aqueous solution containing the APM and the N-[N-(3,3-dimethylbutyl)-L-α-aspartyl]-L-phenylalanine methyl ester to column chromatography using a non-polar, porous polymer-based resin to separate the APM from the N-[N-(3,3-dimethylbutyl)-L-α-aspartyl]-L-phenylalanine.

DETAILED DESCRIPTION OF THE PREFERRED EMBODIMENTS

In order to solve the problem and achieve the object in the present invention, the present inventors have surprisingly discovered that APM can be easily and efficiently separated from N-(3,3-dimethylbutyl)-APM, and thus these two compounds can be each separated and purified at a high purity, from an aqueous solution containing the APM and the APM derivative, or the like by passing such aqueous solution or the like through column chromatography with the use of nonpolar highly porous polymer resin utilizing differences in affinity between them to nonpolar highly porous polymer resin used in the chromatography. Based on the above findings, the present invention has been completed. Thus, the present invention provides to a process for separating and purifying APM and N-[N-(3,3-dimethylbutyl)-L-(α-aspartyl]-L-phenylalanine methyl ester (APM derivative), which entails: subjecting an aqueous solution containing said APM and said APM derivative, or the like to column chromatography with the use of a nonpolar highly porous polymer based resin to separate the APM from the APM derivative.

In the column chromatography operation, for example, an aqueous solution containing above-mentioned two types of compounds may be passed through the column filled with the above-mentioned resin effect separation of each other for purification of each compound, using known methodologies utilizing the differences between the above-mentioned two compounds in affinity to the resin, and specifically the property that APM is weak in affinity to the resin as compared to the APM derivative.

Now, a process of column chromatography, wherein the above-mentioned resin may be used in the form of mixture with another carrier or in combination with another carrier, is used by the present invention, however, the operation for the column chromatography must the above-mentioned resin filled in the column to effectively separate APM from the APM derivative in the mixture thereof.

In the present invention, the following aspects are also entailed:

1. The above process, wherein said nonpolar highly porous polymer based resin contains an aromatic polymer based resin or is an aromatic polymer based resin.

In this case, the above-mentioned aromatic polymer based resin used as the nonpolar highly porous polymer based resin may be employed for all the nonpolar highly porous polymer based resin contained in the column or for a part thereof, and these methods of using the resin are all involved in the present invention.

2. The above process, wherein said aromatic polymer based resin contains at least one resin selected from the group consisting of DIAION SP resin and DIAION HP resin.

3. The above process, wherein said DIAION SP resin contains at least one resin selected from the group consisting of DIAION SP 850 and DIAION SP 207.

4. The above process, wherein said DIAION HP resin contains DIAION HP 20 resin.

As used herein, "DIAION" used for the carrier filled in the column is a trade name of Mitsubishi Chemical Corporation, and a carrier which may be essentially the same resin to any such DIAION in chemical constitution or composition and may have the same action to that of any such DIAION may be contained in the carrier having the above-mentioned trade name, even though it may not have such above trade name for the carrier.

5. In a process for production of N-(3,3-dimethylbutyl)-APM from APM as a starting material, the process for production of said APM derivative, i.e., N-(3,3-dimethylbutyl)-APM, wherein the APM or the fraction including APM separated and purified in any above process is used for said starting material of APM or a part thereof.

In this case, the process for the production as such is not particularly limited, and for its production, a process for production thereof in the reaction for reductive alkylation of APM with 3,3-dimethylbutylaldehyde is enumerated, for example.

6. An APM or an APM derivative obtained in the above process for the separation and purification in the present invention, or produced by being separated and purified using the above process.

7. A sweetener containing the above-mentioned APM derivative, or the above-mentioned APM derivative and a carrier usable for sweeteners, if required, and a process for imparting sweetness, comprising the step of: using the APM derivative for a material requesting sweetness, such as food.

DETAILED DESCRIPTION OF THE PREFERRED EMBODIMENTS

The present invention is directed to a process for obtaining high purity APM and high purity N-(3,3-dimethylbutyl)-APM by separating and purifying each other utilizing differences between such two compounds in affinity to the nonpolar highly porous polymer based resin, in the separation of APM from N-(3,3-dimethylbutyl)-APM to purify each compound thereof from an aqueous solution (water based solution) containing the APM and the APM derivative, or the like, and particularly from the aqueous solution thereof.

The aqueous solution, or the like used for the starting material in the present invention may be in the form of the aqueous solution, or in the form of any solution which may be substantially the same solution thereto on an application to the column chromatography employed in the present invention. For the above-mentioned aqueous solution, for example, a water solution, a solution obtained from solvents which are dissolved or can be dissolved in water, such as methanol, ethanol, isopropyl alcohol, tetrahydrofuran and the like, which may include a solution obtained from a mixed solvent containing plural organic solvents which are dissolved or can be dissolved in water, and a solution obtained from a mixed solvent of water and such a solvent or such a mixed solvent selected from the organic solvents which are dissolved or can be dissolved in water are enumerated.

In the process for separating and purifying them in the present invention, it is desirable to operate the column chromatography according to the conventional or ordinal methods therefor. For example, a preferred operation is carried out by filling the nonpolar highly porous polymer resin in the column, and then passing through the column, preferably an aqueous solution containing APM and N-(3,3-dimethylbutyl)-APM to obtain a part of APM present as contained in the break through solution from the column, and further passing an appropriate eluting solvent (eluent) through the column to elute APM and N-(3,3-dimethylbutyl)-APM in this order.

For the aqueous solution containing APM and N-(3,3-dimethylbutyl)-APM, for example, a water solution obtained by substituting water for a solvent in the reaction solution obtained from the reductive alkylation of APM or a derivative of APM (for example, the derivative wherein the carboxyl group at the β-position of the Asp residue in the APM is protected with a benzyl ester moiety) to produce N-(3,3-dimethylbutyl)-APM, a water solution which has dissolved the crude crystals of the product given from the reaction solution, the mother liquor therefrom or the like is cited. In addition thereto, any aqueous solutions which may contain both APM and N-(3,3-dimethylbutyl)-APM can be applied to the process in the present invention.

A concentration of APM or/and N-(3,3-dimethylbutyl)-APM in the aqueous solution is not particularly limited. An aqueous solution thereof in a concentration of about 0.1 to 1.5 g/dl is desirable for the separation and purification thereof. For the nonpolar highly porous polymer based resin used in the present invention, any resin which may be known as the nonpolar highly porous polymer based resin or the nonpolar highly porous polymer resin, or which may be essentially the same resin in structure or in function thereto may be employed. Among them, an aromatic polymer based resin is preferably employed, and for example, those made of the polymer of styrene and divinylbenzene, such as DIAION HP 20, HP 21, SP 206, SP 207, SP 825, SP 850 and the like, which are all trade names and produced in Mitsubishi Chemical Corporation, Japan, may be used. Any resin chemically equivalent thereto may be used.

As used herein, the aromatic polymer based resins preferably employed in the present invention DIAION HP 20, HP 21, SP 207, SP 825, and SP 850, may be better understood by reference to the following Table 1:

TABLE 1

| Type | HP20 | HP21 | SP825 | SP850 | SP207 |
|---|---|---|---|---|---|
| Chemical Structure | —CH$_2$—CH—CH$_2$—CH— (phenyl, phenyl-CH$_2$CH—) | | | | —CH$_2$—CH—CH$_2$—CH— (phenyl-CH$_2$CH—, phenyl-Br) |
| Apparent density (g/L-R) | 680 | 625 | 690 | 670 | 708 |
| Water content (%) | 55–65 | 45–55 | 52–62 | 46–52 | 43–53 |
| Particle size (>250 μm) | | | | >90% | |
| Effective size(mm) | | | | >0.25 | |
| Uniformity Coefficient | | | | <1.6 | |
| Porosity data pore volume (mL/g) | 1.3 | 1.1 | 1.4 | 1.2 | 1.3 |
| surface area (m2/g) | 600 | 570 | 1000 | 1000 | 600 |
| pore radius (Å) | >200 | 80 | 57 | 38 | 110 |

Regarding the quantity of the resin used, for example, in the case of DIAION SP 207 or DIAION SP 850, it is sufficient that the resin may be employed in a volume of about 0.1 times (1/10) the volume of the aqueous solution in a concentration of N-(3,3-dimethylbutyl)-APM therein having about 1 g/dl. For the eluting solvent (eluent), water, alcohols such as methanol, ethanol, isopropyl alcohol, etc., a mixed solvent containing water and at least one alcohol at an any ratio optionally selected and the like are enumerated. For example, at the time of the operation for adsorption utilizing the aqueous solution containing APM and N-(3,3-dimethylbutyl)-APM, a part of APM present may be obtained in the break through solution from the column, and thereafter APM is obtained by the elution with water as the eluting solvent, and furthermore N-(3,3-dimethylbutyl)-APM is eluted from the column by the elution with alcohol (s) or a mixed solvent containing water and at least one alcohol as the eluting solvent. Accordingly, APM can be separated from N-(3,3-dimethylbutyl)-APM and also each compound can be separated and purified by taking properly fractional collections from the eluted solution.

The eluted solution containing either APM or N-(3,3-dimethylbutyl)-APM thus collected, may be recovered for each compound in the form of the solution and may be used directly for the each compound again, or from the solution, further the crystals for each compound at a high purity may be obtained by known purifying means such as concentration, crystallization and the like, where necessary, from the solution.

Now, a nonpolar highly porous polymer resin is lowered in adsorptive power when the operations for separation with the use of the resin are carried out about 30 times. In such case, an operation for regeneration of the resin used is needed. For regeneration, for example, the resin used and to be reproduced may be washed with a mixed solution consisting of the same quantity of two solutions obtained from 50% by volume of water alcohol solution and 1 mol/l sodium hydroxide (caustic soda) aqueous solution, i.e., a volume ratio of 1:1. In these regeneration methods, the resin can be used again and repeatedly.

There is no difficulty, when N-(3,3-dimethylbutyl)-APM separated and purified, or produced in the process of the present invention is used for a sweetener or food additive or in the production thereof. For example, known methods for production of sweeteners or food additives or for use thereof can be applied in such case using conventional amounts of APM or the APM derivative.

The present invention will now be further illustrated by reference to the certain examples, which are provided solely for purposes of illustration and are not intended to be limitative.

EXAMPLE 1

1.57 g of APM (aspartame) and 1.58 g of N-(3,3-dimethylbutyl)-APM were dissolved in water to prepare a 200 ml of solution, and the solution was passed through the column of 1.6 cm in diameter and 20 cm in height, filled with 20 ml by volume in water of DIAION SP 207, produced by Mitsubishi Chemical Corporation, Japan, to adsorb the APM and the N-(3,3-dimethylbutyl)-APM thereto. At the time of this operation, a part of APM was eluted in the break through solution from the column. Next, APM was eluted using 140 ml of water as the eluting solvent. Further, N-(3,3-dimethylbutyl)-APM was eluted using 30% by volume of methanol aqueous solution (300 ml) and then methanol (100 ml). Now, at the time of the adsorption and the elution, the operations were carried out in the space velocity SV=2. In a series of operations, the fractions collected from 100 to 200 ml of the break through solution from the column (solution which flowed through the column without using eluting solvent) and all the eluted solution with the elution using water as the eluting solvent were obtained for the eluate of APM, and the fractions collected from the 100 to 300 ml of the eluted solution with the elution using 30% by volume of methanol aqueous solution as the eluting solvent and all the eluted solution with the elution using methanol as the eluting solvent were obtained for the eluate of N-(3,3-dimethylbutyl)-APM. In the analysis of each eluted solutions (eluates) by the HPLC (High Performance Liquid Chromatograph), the eluate of APM contained 1.43 g of APM yielding 91%, and however did not contain any (3,3-dimethylbutyl)-APM. The eluate of the (3,3-dimethylbutyl)-APM contained 1.35 g of (3,3-dimethylbutyl)-APM yielding 86%, and however contained no APM.

EXAMPLE 2

The same operation as that in the Example 1 was carried out, except that all the solutions eluted with 30% by volume of methanol aqueous solution and eluted with the methanol were collected for the eluate of N-(3,3-dimethylbutyl)-APM, and thereby the eluate of N-(3,3-dimethylbutyl)-APM was obtained. In the analysis thereof by the high performance liquid chromatography, this eluate contained 1.58 g of N-(3,3-dimethylbutyl)-APM yielding 100% and a trace quantity of APM, corresponding to 9.3% by weight of APM per N-(3,3-dimethylbutyl)-APM.

The thus obtained eluate of N-(3,3-dimethylbutyl)-APM was concentrated under reduced pressure to a solid material. To the resulting residue, 15 ml of water and a trace quantity of methanol were added to dissolve it, and then the solution was subjected to the crystallization at a temperature of 5° C. overnight. Thus obtained crystals were separated by filtration and dried under reduced pressure to obtain 1.24 g of the dried crystals. In the analysis thereof by the high performance liquid chromatography, these crystals contained 1.22 g (yield: 77%) of N-(3,3-dimethylbutyl)-APM in the purity of 99.0%. In the analysis by Karl Fischer's method, the water content in the crystals was 1.6% by weight.

COMPARATIVE EXAMPLE 1

To 1.51 g of APM and 1.54 g of N-(3,3-dimethylbutyl)-APM, 50 ml of water were added to dissolve them, and then the resulting solution was subjected to the crystallization at a temperature of 5° C. overnight. Thus obtained crystals were separated by filtration, washed with 50 ml of water and dried under reduced pressure to obtain 1.83 g of the dried crystals. In the analysis by the high performance liquid chromatography, these crystals contained 0.78 g of APM and 0.98 g of N-(3,3-dimethylbutyl)-APM. In the analysis by Karl Fischer's method, the water content in the crystals was 3.9% by weight.

EXAMPLE 3

3.45 g of APM and 1.70 g of N-(3,3-dimethylbutyl)-APM were dissolved in water to obtain 400 ml of solution. The solution was passed through the column same to that used in the Example 1, filled with 20 ml by volume in water of DIAION SP 207, produced by Mitsubishi Chemical Corporation, Japan to adsorb the APM and the N-(3,3-dimethylbutyl)-APM thereto. At the time of this operation, a part of APM was eluted in the break through solution from the column. Next, APM was eluted with the elution using 160 ml of water as the eluting solvent. Further, N-(3,3-dimethylbutyl)-APM was eluted with the elution using 60% by volume of methanol aqueous solution (400 ml). Now, at the time of the adsorption and the elution, the operations were carried out in the space velocity SV=1.5. In a series of operations, the fractions collected from 130 to 400 ml of the break through solution from the column (, solution which flowed through the column without using eluting solvent) and all the eluted solution with the elution using water as the eluting solvent was obtained for the eluate of APM, and all the eluted solution with the elution using 60% by volume of methanol aqueous solution as the eluting solvent were obtained for the eluate of the N-(3,3-dimethylbutyl)-APM.

In the analysis of each solution eluted (each eluate) by the high performance liquid chromatography, the eluate of APM contained 3.38 g (yield: 98%) of APM, and however did not contain N-(3,3-dimethylbutyl)-APM. The eluate of the N-(3, 3-dimethylbutyl)-APM contained 1.70 g (yield: 100%) of N-(3,3-dimethylbutyl)-APM, and a trace quantity of APM (4.1% by weight of APM per N-(3,3-dimethylbutyl)-APM).

EXAMPLE 4

1.01 g of APM and 1.93 g of (3,3-dimethylbutyl)-APM were dissolved in water to prepare 230 ml of solution. The solution was passed through the column same to that used in the Example 1, filled with 20 ml by volume in water of DIAION SP 850, produced by Mitsubishi Chemical Corporation, in Japan, to adsorb the APM and the (3,3-dimethylbutyl)-APM. At the time of this operation, a part of APM present was eluted in the break through solution from the column. Next, APM was eluted with elution using 160 ml of water as the eluting solvent. Further, N-(3,3-dimethylbutyl)-APM was eluted with the elution using 30% by volume of isopropyl alcohol aqueous solution (300 ml). Now, at the time of the adsorption and the elution, the operations were carried out in the space velocity SV=2. In a series of operations, the fractions collected from 130 to 230 ml of the break through solution from the column (solution which flowed through the column without using the eluting solvent) and all the solution eluted with the elution using water as the eluting solvent (agent) were obtained for the eluate of APM. Further, all the solution eluted with the elution using 30% by volume of isopropyl alcohol aqueous solution was collected for the eluate of the N-(3,3-dimethylbutyl)-APM. In the analysis of each solution eluted by the high performance liquid chromatograph, the eluate of APM contained 0.873 g (yield: 86%) of APM, and however did not contain (3,3-dimethylbutyl)-APM. The eluate of the N-(3,3-dimethylbutyl)-APM contained 1.93 g (yield: 100%) of N-(3,3-dimethylbutyl)-APM and a trace quantity of APM (7.1% by weight of APM per N-(3,3-dimethylbutyl)-APM).

EXAMPLE 5

2.06 g of APM and 1.99 g of N-(3,3-dimethylbutyl)-APM were dissolved in water to prepare 230 ml of solution. The solution was passed through the column same to that used in the Example 1, filled with 20 ml by volume in water of DIAION SP 850, produced by Mitsubishi Chemical Corporation, Japan, to adsorb the APM and the N-(3,3-dimethylbutyl)-APM. At the time of this operation, a part of APM was eluted in the break through solution from the column. Next, APM was eluted with the elution using 200 ml of water as the eluting solvent. Further, N-(3,3-dimethylbutyl)-APM was eluted with the elution using 20% by volume of methanol aqueous solution (200 ml) and then methanol (100 ml), respectively as the eluting solvents. Now, at the time of the adsorption and the elution, the operations were carried out in the space velocity SV=2. In a series of operations, the fractions collected from 120 to 230 ml of the break through solution from the column (solution which flowed through the column without using an eluting solvent) and all the solution eluted with elution using water as the eluting solvent were obtained for the eluate of APM, and the fractions collected from 60 to 200 ml of the eluted solution with the elution using 20% by volume of methanol aqueous solution and all the solution eluted with the elution using methanol, respectively as the eluting solvents were obtained for the eluate of the N-(3,3- dimethylbutyl)-APM. In the analysis of each solution eluted by the high performance liquid chromatography, the eluate of APM contained 2.02 g (yield: 98%) of APM, and however did not contain N-(3,3-dimethylbutyl)-APM. The eluate of the N-(3,3-dimethylbutyl)-APM contained 1.83 g (yield: 92%) of N-(3,3-dimethylbutyl)-APM, and none of APM.

EXAMPLE 6

The same operation as that in the Example 5 was carried out except, that all the solutions eluted with the elution using 20% by volume of methanol aqueous solution and eluted with the elution using methanol in the Example 5, were collected for the eluate of N-(3,3-dimethylbutyl)-APM, and thereby the eluate of N-(3,3-dimethylbutyl)-APM was obtained. In the analysis thereof by the high performance liquid chromatography, this eluate contained 1.99 g (yield: 100%) of N-(3,3-dimethylbutyl)-APM and a trace quantity of APM (2.3% by weight of APM per N-(3,3-dimethylbutyl)-APM.

EXAMPLE 7

APM (67.4 g, 0.220 mol) in the water content of 3.9%, 3,3-dimethylbutylaldehyde (25 ml, 0.199 mol) and 5% palladium-carbon (20 g) were reacted in a mixed solvent of methanol (300 ml) and 0.1 M acetic acid aqueous solution (400 ml) at room temperature under a stream of hydrogen ($H_2$) for 4 hours. In the analysis of the reaction solution by the thin layer chromatography, N,N-di-(3,3-dimethylbutyl)-APM was not detected. Next, the reaction solution was heated to dissolve the crystals undissolved, and the catalyst was removed by filtration to obtain 922 ml of the reaction solution. In the analysis thereof by the high performance liquid chromatography, the solution contained 30.6 g of APM and 35.4 g of N-(3,3-dimethylbutyl)-APM.

Thus obtained reaction solution (520 ml) was concentrated under reduced pressure to remove methanol. The residue was dissolved in water to prepare 2000 ml of the solution, and the solution was passed through the column of 5.0 cm in diameter and 30 cm in height, filled with 200 ml by volume in water of DIAION SP 850, produced by Mitsubishi Chemical Corporation, Japan, to adsorb the APM and the N-(3,3-dimethylbutyl)-APM. At the time of this operation, a part of APM present was eluted in the break through solution from the column. Next, APM was eluted with the elution using 2000 ml of water as the eluting solvent. Further, N-(3,3-dimethylbutyl)-APM was eluted with the elution using 20% by volume of methanol aqueous solution (700 ml) and then methanol (1000 ml) as the eluting solvents, respectively. Now, at the time of the adsorption and the elution, the operations were carried out in the space velocity SV=2. In a series of operations, the fractions collected from the 1200 to 2000 ml of the break through solution from the column (the solution which flowed through the column without using an eluting solvent) and all the solution eluted with the elution using water as the eluting agent were obtained for the eluate of APM, and all the solution eluted with the elution using methanol as the eluting solvent was obtained for the eluate of the N-(3,3-dimethylbutyl)-APM. In the analysis of each solution eluted by the high performance liquid chromatography, the eluate of APM contained 16.9 g (yield: 98%) of APM, and however did not contain N-(3,3-dimethylbutyl)-APM. The eluate of the N-(3,3-dimethylbutyl)-APM contained 18.8 g (yield: 94%) of N-(3,3-dimethylbutyl)-APM, and however contained none of APM.

EXAMPLE 8

The eluate of the N-(3,3-dimethylbutyl)-APM obtained in the Example 7, was concentrated under reduced pressure to a solid material. To the residue, water (180 ml) and a small amount of methanol were added to dissolve it. The resulting solution was subjected to the crystallization at a temperature of 5° C. overnight, and thus obtained crystals were separated by filtration, and dried under reduced pressure to obtain 14.3 g of the dried crystals. In the analysis thereof by the high performance liquid chromatography, the crystals contained 14.1 g (yield: 75%) of N-(3,3-dimethylbutyl)-APM in the purity of 99.5%. In the analysis by Karl Fischer's method, the water content in the crystals was 1.1% by weight.

EXAMPLE 9

The eluate of APM obtained in the Example 7, was concentrated under reduced pressure to prepare a solution having 470 ml in a liquid volume. Thus obtained solution was heated to dissolve the crystals partially precipitated therein, and then subjected to the crystallization at a temperature of 5° C. while standing overnight. Thus obtained crystals were separated by filtration and dried under reduced pressure to obtain 14.3 g of the dried crystals. In the analysis thereof by the high performance liquid chromatography, the crystals contained 13.9 g (yield: 82%) of APM in the purity of 99.8%. In the analysis by Karl Fischer's method, the water content in the crystals was 3.0% by weight.

Finally, as used herein, the terms "nonpolar" and "porous" are used in accordance with their known definitions in polymer chemistry, and are distinguished from polymer based resins which are neither porous nor nonpolar.

In accordance with the present invention, APM can be separated easily and efficiently from N-(3,3-dimethylbutyl)-APM, i.e. APM derivative, and thus they can be each purified at a high purity, from an aqueous solution containing the APM and the APM derivative, or the like by subjecting such aqueous solution or the like to the above-mentioned column chromatography with the use of a nonpolar highly porous polymer based resin.

Having described the present invention, it will now be apparent that many changes and modifications may be made to the above embodiments without departing from the spirit and scope of the present invention.

What is claimed is:

1. A process for separating and purifying aspartame (APM) and N-(3,3-dimethylbutyl)-L-(α-aspartyl)-L-phenylalanine methyl ester (N-(3,3-dimethylbutyl)-APM), which comprises the step of:

subjecting an aqueous-based solution containing said APM and the N-(3,3-dimethylbutyl)-APM to column chromatography by effecting said column chromatography with a nonpolar, porous polymer based resin, thereby separating the APM from the N-(3,3-dimethylbutyl)-APM, wherein said nonpolar, porous polymer based resin is an aromatic polymer based resin.

2. The process of claim 1, wherein said aromatic polymer based resin is obtained from monomers containing styrene and divinylbenzene, which are each optionally substituted.

3. The process of claim 1, wherein said aromatic polymer based resin is substituted by hydrophobic substituents.

4. The process of claim 3, wherein said hydrophobic substituents are selected from the group consisting of bromine and a bromine-containing substituent group.

5. The process of claim 1, wherein water, alcohol, tetrahydrofuran or a mixture thereof is used as an eluting solvent for said column chromatography.

6. The process of claim 5, wherein water is used as the eluting solvent.

7. The process of claim 5, wherein alcohol or a mixture thereof with water is used as the eluting solvent.

8. The process of claim 1, wherein said nonpolar based resin contains a resin having a pore size of more than 100 Å.

9. The process of claim 1, wherein said aqueous-based solution has a concentration of APM or N-(3,3-dimethylbutyl)-APM or both of from about 0.1 to 1.5 g/dl.

10. The process of claim 7, wherein said alcohol is methanol, ethanol or isopropyl alcohol.

11. The process of claim 10, wherein said alcohol is methanol.

12. The process of claim 1, wherein said N-(3,3-dimethylbutyl)-APM is obtained as an eluate.

13. The process of claim 12, which further comprises crystallizing said N-(3,3-dimethylbutyl)-APM at a purity of at least 99.0%.

14. The process of claim 13, wherein said crystallized N-(3,3-dimethylbutyl)-APM has a water content of 3.0% by weight or less.

* * * * *